United States Patent [19]

Rothfuss

[11] Patent Number: 4,592,354

[45] Date of Patent: Jun. 3, 1986

[54] TISSUE RETENTION SPOOL FOR INTRALUMINAL ANASTOMOTIC SURGICAL STAPLING INSTRUMENT AND METHODS

[75] Inventor: Robert G. Rothfuss, Bellevue, Ky.

[73] Assignee: Senmed, Inc., Cincinnati, Ohio

[21] Appl. No.: 540,895

[22] Filed: Oct. 11, 1983

[51] Int. Cl.⁴ ............................................. A61B 17/04
[52] U.S. Cl. ................................ 128/305; 128/334 R
[58] Field of Search .............. 128/305, 334 R, 334 C

[56] References Cited

U.S. PATENT DOCUMENTS

| | | | |
|---|---|---|---|
| 2,940,451 | 6/1960 | Vogelfanger et al. | 128/334 |
| 3,193,165 | 7/1965 | Akhalaya et al. | 128/305 X |
| 3,388,847 | 6/1968 | Kasulin et al. | 128/334 X |
| 3,552,626 | 1/1971 | Astafiev et al. | 128/334 X |
| 3,593,903 | 7/1971 | Astafiev et al. | 128/305 X |
| 3,606,888 | 9/1971 | Wilkinson | 128/334 |
| 3,638,652 | 2/1972 | Kelley | 128/305 |
| 4,207,899 | 7/1980 | Becht | 128/305 |
| 4,306,373 | 12/1981 | Chatani et al. | 446/124 |
| 4,319,576 | 3/1982 | Rothfuss | 128/305 |
| 4,345,600 | 8/1982 | Rothfuss | 128/33 R |
| 4,476,863 | 10/1984 | Kanshin et al. | 128/305 |

*Primary Examiner*—Hugh R. Chamblee
*Attorney, Agent, or Firm*—Wood, Herron & Evans

[57] ABSTRACT

A tissue retention spool is disposed on the anvil actuating rod of an intraluminal anastomotic surgical stapling instrument. Tubular tissue is gathered and held on the spool by a suture tie, thus eliminating the previously required purse-stringing procedure. The spool and rod are constructed to initially resist relative sliding motion as the spool is withdrawn into the staple carrier/cylindrical scalpel area prior to setting of staples and internal tissue excision. The combined spool and instrument serve to hold tubular tissue in an erect, closed condition, facilitating the use of closed surgical techniques, without purse-stringing, in limited access areas such as lower colon resections. Alternative spools and methods are included.

12 Claims, 13 Drawing Figures

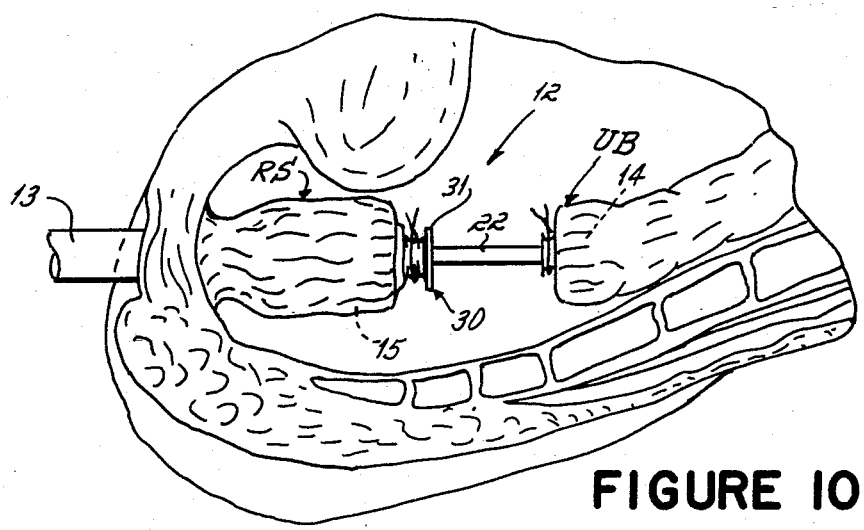
FIGURE 10
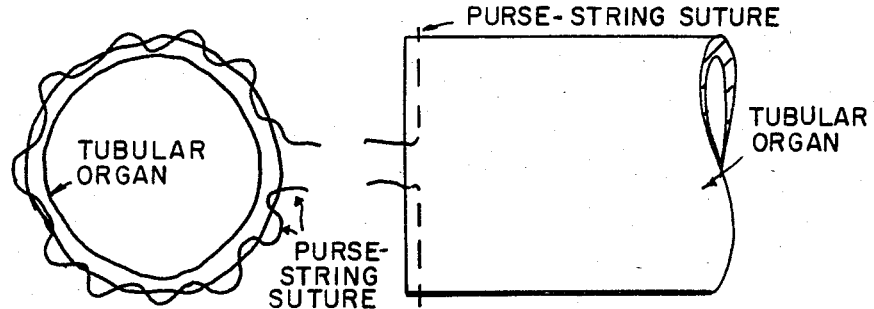
FIGURE 11A
FIGURE 11B

TISSUE RETENTION SPOOL FOR INTRALUMINAL ANASTOMOTIC SURGICAL STAPLING INSTRUMENT AND METHODS

This invention relates to intraluminal anastomotic surgical stapling instruments and more particularly to improved apparatus and methods for securing and stapling together remaining portions of transected tubular tissues and organs.

In recent years, there has been a steady increase in the use of intraluminal staplers in surgical procedures involving the alimentary canal, from the esophagus to the anus.

Intraluminal circular staplers, of the type such as those disclosed in U.S. Pat. Nos. 4,207,898 and 4,319,576 produce a result generally superior to hand-placed sutures. These apparatus considerably reduce the time required to perform the procedure as compared to the hand-placing of sutures.

In the use of intraluminal circular staplers, it is current practice to secure tubular tissue, such as a bowel, to the stapler before the bowel is stapled together. This is accomplished by placing a purse-string suture in the bowel end and drawing up the end of the bowel around the stapler rod by tightening the purse-string suture.

Purse-string sutures are placed in the bowel end by hand, or by the use of a purse-stringer apparatus of the type disclosed in U.S. Pat. No. 4,345,600. While this type apparatus is of great assistance in placing purse-string sutures, tissue which is too thick or too thin may cause a malfunction such as a missed stitch or a stitch too shallow to hold. If these conditions are not corrected prior to setting the staples and excising the excess internal tissue from the organ, a leaky and non-hemostatic anastomotic can result.

Moreover, the purse-stringer apparatus is very difficult to use in certain procedures where organ access is difficult, such as in certain low colon resections. In such cases, it is not possible to use a purse-stringer, and it is extremely difficult and time consuming to place the purse-string suture by hand. Also, and for these above reasons, it is difficult to make use of a "closed technique" in this limited access situation.

Still further, in such difficult access procedures as a low colon resection, it is frequently necessary to utilize rectal stump retention sutures to hold the rectal stump up and erect for further suturing. These retention sutures can slip or tear out, and are otherwise bothersome as being in the way.

Accordingly, it has been one objective of this invention to provide an improved intraluminal anastomotic surgical stapling instrument.

A further objective of this invention has been to provide improved apparatus and methods for securing tubular tissue to a circular stapling instrument.

A further objective of the invention is to provide apparatus and methods for at least partially eliminating the purse-stringing procedure in a tubular tissue anastomotic procedure.

A further objective of the invention has been to facilitate the use of an intraluminal anastomotic surgical stapling instrument in limited access areas.

A further objective of the invention has been to enable the use of a "closed technique" surgical procedure in a limited access area where it is otherwise either unsuitable or extremely difficult, tedious and time consuming.

A still further objective of the invention has been to provide improved apparatus and methods whereby an intraluminal anastomotic surgical stapling instrument can itself be used to hold a rectal stump in place and thus eliminate the need for retention sutures.

To these ends, and according to a preferred embodiment of the invention, an intraluminal anastomotic surgical stapling instrument, of the type disclosed in U.S. Pat. No. 4,319,576, is provided with a tissue retention means, such as a flanged spool, yieldably disposed on the instrument rod between the anvil and the cartridge. The spool flanges are of lesser diameter than the cylindrical scalpel provided in the instrument.

The instrument is inserted into tubular tissue, such as a bowel, and the bowel is drawn radially inwardly by means of wrapping, tying and tightening a suture, or some other means such as a plastic tie, around the bowel at the spool. The tissue is secured to the spool by the suture or tie, with the spool flanges facilitating tissues retention. Thereafter, the bowel is cut adjacent the spool's forward flange, with the lower bowel being retained about the spool by the wrapped suture.

The upper bowel is then transected and the remaining bowel end portion is brought into position over the distal end of the instrument. Since this end is usually freely accessible, a purse-string suture is mechanically applied and the end is secured over the anvil and about the rod adjacent the spool.

Thereafter, the anvil is drawn toward the staple driving cartridge while the spool and secured bowel end move along the rod and into the area surrounded by the cartridge and the cylindrical scalpel. Once the anvil is properly placed relative to the staple cartridge, the instrument is activated to implant the staples and move the scalpel forward around the spool, cutting off tissue within the lumen of the bowel interiorly of the circular staple line. This leaves tissue "doughnuts" surrounding the spool and the rod, and this tissue is removed with the instrument as it is withdrawn.

In an alternative embodiment, two spools of appropriate width could be mounted on the instrument rod, one spool for securing the end of the proximal organ and one for securing the end of the distal organ.

In yet another embodiment, a washer or flange is provided as a part of the staple anvil for attachment of the end of the distal organ internally of the staple anvil.

The invention provides a number of improvements and advantages. It eliminates the purse-stringing requirements for at least the proximal organ end, and secures that end for stapling in a more consistently uniform manner. This greatly facilitates use of the stapling instrument in limited access areas, while at the same time improving the closure result and permitting the use of a "closed technique" even when dealing with a lower colon resection. Also in this connection, the invention serves to eliminate the need for using retention sutures for the rectal stump and renders the instrument itself usable to hold the stump in place.

Accordingly, use of an intraluminal anastomotic surgical stapling instrument is enhanced, surgical procedures are improved, and a great deal of time and tedious procedure techniques are saved and eliminated, while the uniformity of final tissue anastomotic is improved.

These and other objectives and advantages will become even more readily apparent from the following detailed description of a preferred embodiment of the invention and from the following drawings in which:

FIG. 10 is cross sectional view illustrating the utilization of the invention in a limited access area; and FIGS. 11A and 11B are respective end and longitudinal views of a tubular structure and a purse-string suture associated therewith.

Figure 1:
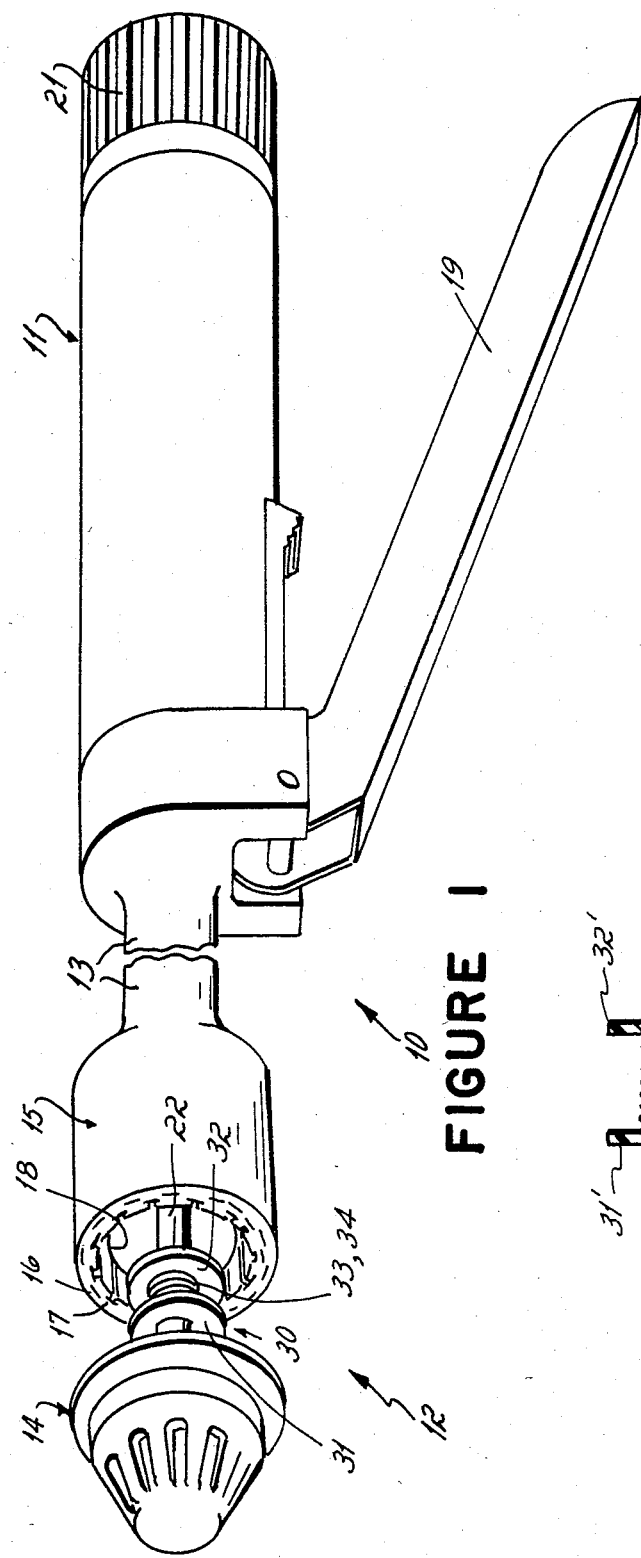
FIG. 1 is a perspective view of an ILS instrument modified according to a preferred embodiment of the invention.

Turning now to the drawings, there is shown in FIG. 1 an intraluminal anastomotic surgical stapling instrument 10. For purposes of brevity in the following description, the intraluminal anastomotic surgical stapling instrument 10 will be referred to as an "ILS" instrument 10. The ILS instrument 10 used in connection with this invention is illustrated and described in U.S. Pat. No. 4,319,576, which for purposes of disclosure is incorporated herein by reference.

The ILS instrument 10 is particularly useful for the anastomotic of transected tubular tissue structures such as body organs, and including but not limited to, the esophagus, stomach and bowel, and is generally used as described in the aforesaid U.S. Pat. No. 4,319,576 for stapling transected organs together.

The preferred embodiment of this invention constitutes an improvement to instruments of the type illustrated at 10, and provides an improved method for the anastomotic or joining by stapling of transected tubular tissues, such as those mentioned above.

Since ILS instrument 10 is disclosed in detail in U.S. Pat. No. 4,319,576, only a very brief description its operation and structure is necessary here. In particular, ILS instrument 10 includes a handle or proximate end portion 11 and a distal or operative end portion 12, separated by an elongated shank 13. Shank 13 serves to mount the operative end 12 away from the handle 11, and provides a housing for control members which extend between the operative end 12 and the proximate end 11.

Figure 3:
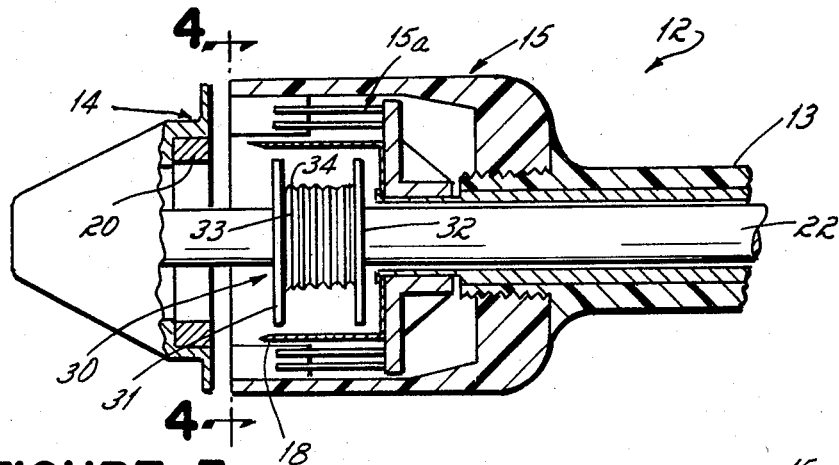
FIG. 3 is a more detailed cross sectional view of the staple cartridge, anvil and tissue retention spool of the instrument as shown in FIG. 1.
Figure 4:
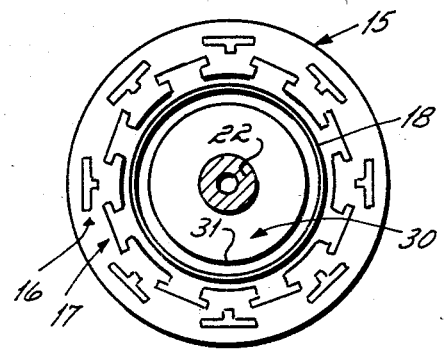
FIG. 4 is a cross sectional view taken along lines 4—4 of FIG. 3.

As perhaps best seen in the cross section of FIG. 3, the operative end 12 includes an anvil 14 and a cylindrical staple carrier or cartridge 15 housing the staple driving apparatus 15a. Staple driving apparatus 15a is provided with one or preferably two circular, staggered arrays 16 and 17 of staples as best shown in the cross section of FIG. 4. The arrays 16 and 17 illustrate the disposition of two circular, staggered lines of staples utilized to secure the transected tissues together. Drivers 15a behind the staples can be shifted to drive the staples forwardly through tissue and onto anvil 14 for clinching, as disclosed in U.S. Pat. No. 4,319,576.

A cylindrical scalpel or knife 18 is disposed within the staple cartridge 15 and is shiftable outwardly, upon actuation of the handle 19 at the handle end 11, to engage a washer 20 interiorly of the anvil 14 and excise any tissue therebetween. As noted from the drawings, the staple driving cartridge 15, together with the arrays 16 and 17 and the anvil 14, are generally circular, the anvil providing means for clinching the individual staples as they are driven outwardly of the staple driving cartridge 15, also upon actuation of the handle 19 at handle end 11 of the ILS instrument 10.

Turning briefly to a description of the operation of the ILS instrument as disclosed in U.S. Pat. No. 4,319,576, the anvil 14 is shifted away from the staple cartridge 15 by rotation of a knob 21 at the handle end 11. This can be done before or after the instrument is inserted into an lumen, for example.

Thereafter, and prior to this invention, a purse-string suture (see FIGS. 11A and 11B) was applied to the proximate end of the lumen either by means of a pursestringer such as that shown in U.S. Pat. No. 4,345,600, or manually. The lower end of the lumen was then secured to the rod 22 about the staple cartridge head 15 by drawing up the purse-string suture. Thereafter, the upper end of the lumen was pulled off over the anvil 14 and the diseased portion removed. The lower end of the upper transected lumen was then provided also with a purse-string suture. It was then pulled over the anvil 14 and thereafter gathered around the rod 22 just in front of the anvil 14. Thereafter, the knob 21 was rotated so as to shift the anvil 14 toward the staple cartridge 15. This positioned the anvil 14 in operative relationship with the cartridge 15 to clinch the staples to be driven. Handle 19 was then operated, whereupon the staples were driven into inwardly turned flanges of both the lower and upper lumen, and in the circular arrayed pattern of staggered staple rows. At the same time, the cylindrical knife 18 was driven forward to excise the tissue internally of the staple rows. Once the staples were driven and the tissue excise, the ILS instrument was freed and was withdrawn through the lumen, leaving a rejoined lumen by means of the circular arrays of staples.

When the purse-string suture was applied by hand, or mechanically through use of a purse-stringer as disclosed in U.S. Pat. No. 4,345,600, there was some possibility that a stitch may be missed, or may be placed too shallow to hold, or otherwise would not be secured to the tissue in a uniform manner, such as that shown in FIGS. 11A and 11B. If a stitch was missed or if the stitch was placed too shallow to hold, a portion of the tissue is released and the final stapled anastomotic may not be uniform or secure, but rather could leak. Moreover, there are many occasions where it is necessary to transect a bowel, for example, in a place where access is difficult to obtain. This occurs, for example, in the lower colon and rectal area such as illustrated in FIG. 10, where the lower portion of the bowel to be transected is surrounded by bone and other tissues, making it very difficult for the surgeon to manually place a proper purse-string suture, as shown in FIGS. 11A and 11B, and almost impossible to utilize a purse-stringer as shown in U.S. Pat. No. 4,345,600.

According to a preferred embodiment of the invention, an ILS instrument 10 is modified by the utilization of a tissue retention means located on the rod 22, as shown in FIG. 1, in a position between the anvil 14 and staple cartridge 15. Such a tissue retention means preferably comprises a tissue retention spool 30 which is shown in a number of the drawings.

The tissue retention spool 30 is comprised of two flanges, including a distal flange 31 and a proximate flange 32, separated by a shank member 33. The flanges 31, 32 are of greater diameter than the shank 33, as shown in FIG. 1. In addition, the shank 33 is provided with a plurality of radially extending tissue engaging projections or ridges 34 which enhance the securing of tissue to the spool 30, as is hereinafter described.

These ridges, or projections 34, serve to restrain the tissue against lateral or normal movement with respect to the spool. While various projection heights and widths can be chosen with a view toward the specific tissue in mind, one suitable spool 30 contains a plurality of projections which are approximately 0.040 inches high and which measure about 0.070 inches from crest to crest. It is believed that a preferred range of projection height is approximately 0.030 inches or greater, depending on the type of tissue used. However, different projection heights may be found to be suitable.

It is also noted that the spool 30 has a preferable outside diameter of approximately 0.55 inches and that the spool width from flange to flange is approximately 0.35 inches. Of course, there are different size ILS instrument instruments, depending upon the particular application desired, and spool sizes are adjusted accordingly. For example, and without limitation, certain ILS instrument instruments may be found in the ranges of 21, 25, 29 and 33 millimeters, which is the outside diameter of the staple cartridge 15 at the distal end of the ILS instrument 10.

Preferably, the spool 30 is mounted on the rod 22 in frictional engagement therewith so that the spool 30 tends to remain in a set position on the rod 22, but also so that the spool 30 can be moved along the rod 22 only after the application of a predetermined axial force to the spool 30, or the rod 22 when the spool 30 is held. In this regard, the spool 30 is preferably made from a resilient material. One such material found to be suitable is based on the composition of berylium sulfide and sold by the Shell Oil Company under its trademark, "KRAYTON." Other materials may be useful as well. Such material, when used to form the spool 30 and in conjunction with the metallic rod 22, has been found to provide a sufficient resistance to sliding of the spool along the rod.

It will also be appreciated that the outer diameter of the spool 30, flanges 31 and 32 is at least slightly less than the inside diameter of the cylindrical scalpel 18, so that the spool 30 can be shifted or received within the area surrounded by the cylindrical scalpel 18.

Figure 2:
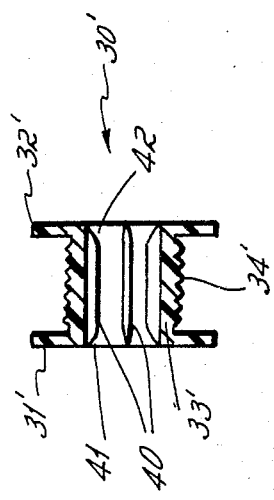
FIG. 2 is a cross sectional view of an alternative tissue retention spool according to the invention.

In an alternative embodiment, a modified spool is utilized, as shown in FIG. 2. The alternative spool includes a plurality of inwardly extending projections 40, having tapered ends 41 and 42. The projections 40 are formed to frictionally engage the rod 22 to provide the desired resistance to sliding of the spool 30 along the rod 22. In FIG. 2, the spool 30 is otherwise similar to that of the preferred embodiment, as indicated by the primed numbers utilized to indicate like parts.

Turning now to FIGS. 5-9, the ILS instrument 10 modified according to the invention is operated as follows.

Figure 5:
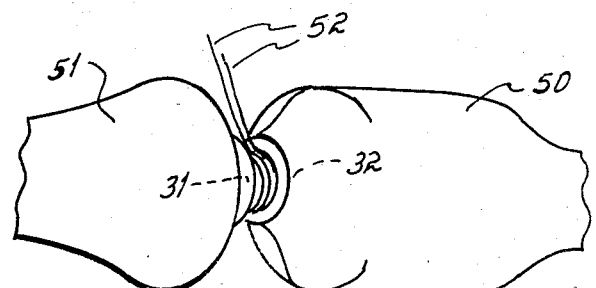
FIG. 5 is a perspective view illustrating the initial step of utilization of the invention of FIG. 1.

First, the ILS instrument 10 is inserted into a tubular tissue structure such as a bowel as shown in FIG. 5. In FIG. 5, a lower bowel 50 and an upper bowel 51 are referred to for illustrative purposes. Prior to or after insertion of the ILS instrument 10 into the bowel 50, the knob 21 of the ILS instrument is operated to extend the anvil 14 away from the staple cartridge 15, thus exposing the spool 30 between the anvil 14 and the stapler cartridge 15.

Figure 5A:
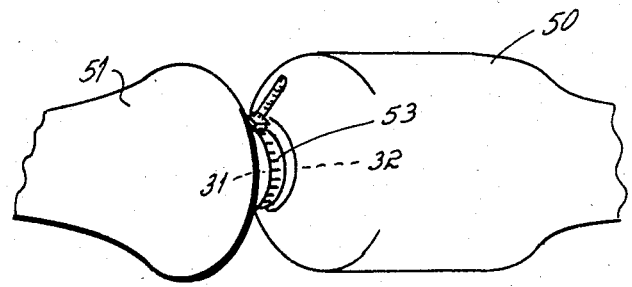
FIG. 5A is a perspective view similar to FIG. 5, but showing an alternative plastic tie securing tissue about the spool.

Once the ILS instrument 10 is inserted to a position below the area to be transected, the surgeon feels for the spool 30 to insure its presence in the open area between the anvil 14 and cartridge 15. He thereafter gathers in and secures the tissue of the bowel around the spool 30 between the flanges 31, 32 and against the projections 34. This can be done by means of a suture 52, which is wrapped around the tissue in the area between the spool flanges 31, 32 and is tightened and tied so as to securely hold the tissue against the spool. No purse-string suture is required, the wrapped suture 52 holding the tissue on the projections 34 of the spool 30. Alternatively, and as shown in FIG. 5A, a clinchable plastic tie 53 could be used in place of the suture. Any other suitable securing means, such as suture 52 or plastic tie 53, could also be used.

Figure 6:
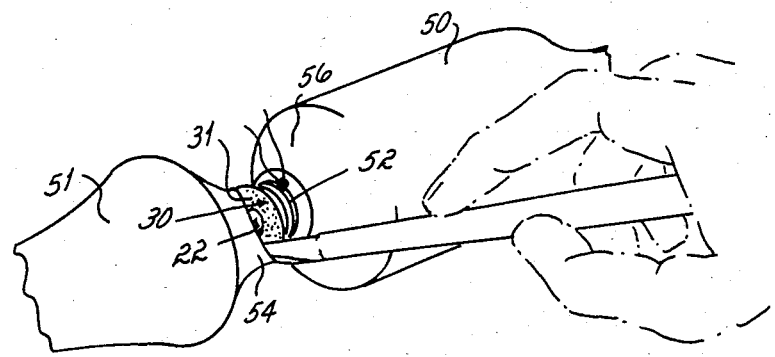
FIG. 6 is a view illustrating the initial excision in tubular tissue with which the invention is used.
Figure 7:
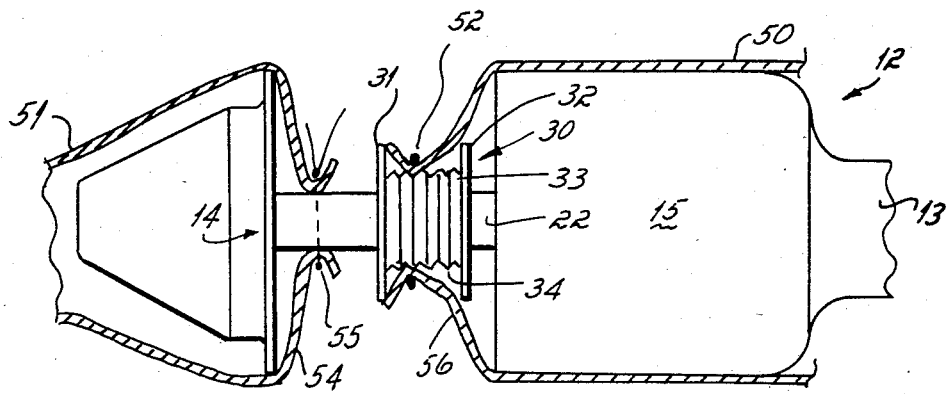
FIG. 7 is a partial cross sectional view showing the instrument of FIG. 1 in extended form prior to the stapling of a transected bowel.

Thereafter, and once the suture has been tied, for example, the upper bowel 51 can be excised from the lower bowel 50, as shown in FIG. 6. The distal spool flange 31 can be used as a cutting guide. It will be appreciated that the suture 52 or plastic tie 53, after this incision is made, retains the upper end of the lower bowel 50 positively on the spool 30. Thereafter, the upper bowel 51 can be removed from the anvil 14 end of the ILS instrument 10 and the upper bowel 51 can be transected to remove a diseased portion, for example. Once the diseased portion has been removed, the transected upper bowel 51, having a lower end 54, is provided with a purse-string suture 55. The end 54 is gathered about the rod 22 of the ILS instrument and over anvil 14. The upper end 56 of the lower bowel 50 remains secured to the spool 30.

At this point, the handle 19 of the ILS instrument is operated to shift the anvil 14 toward the staple cartridge 15 and to a predetermined distance between the anvil 14 and the leading edge of the staple cartridge 15. This is determined by a preliminary measurement of the thickness of the tissue to be joined and may be, for example, on the order of 1 to 3 millimeters, but may be more or less depending on the nature of the tissues to be joined.

Figure 8:
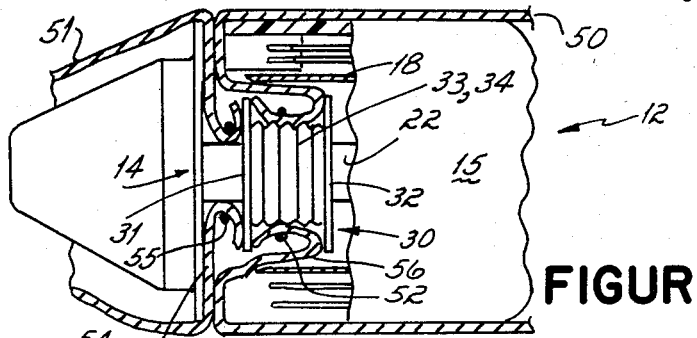
FIG. 8 is a partial cross sectional view of the invention showing the position of the staple cartridge, the anvil and the tissue retention spool immediately prior to stapling of the transected bowel together and the cutting of the internal ends of the transected bowel internally of the circular staple line.

As the anvil 14 is shifted by means of retraction of rod 22 into cartridge 15 and shank 13, when the knob 21 is operated, the anvil 14 pulls the end 54 of the upper bowel 51 in a direction toward the distal flange 31 of the spool 30. The spool 30 is also moved, however, by the rod into the area surrounded by the internal diameter of the cylindrical scalpel 18, all as shown in FIG. 8. Once the spool 30 is so positioned, as in FIG. 8, further inward movement of the rod 22 and anvil 14 is possible since the spool 30 can now slide on rod 22 by virtue of its yieldable friction fit. Movement of the spool 30 into the scalpel 18 area tends to stretch the end 56 of the lower bowel 50 around the forward end of the staple cartridge 15.

Once the anvil 14 has been moved into the predetermined relationship with the staple cartridge 15, the handle 19 is operated to drive staples through the two layers of tissue between the staple cartridge 15 and the anvil 14. At the same time, the cylindrical scalpel 18 is driven forwardly to excise the bowel tissue internally from rod 22. This leaves a ring or doughnut of bowel tissue ends on rod 22 and spool 30.

Figure 9:
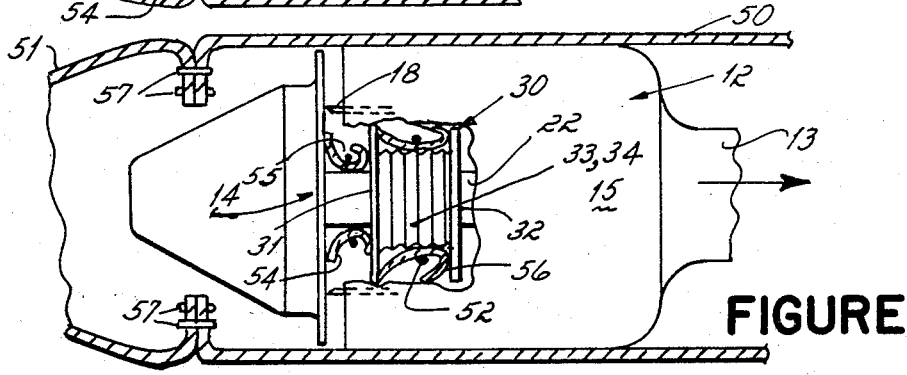
FIG. 9 is a cross sectional view showing removal of the instrument from the anastomotic of a transected bowel.

Accordingly, a circular array of staples, such as illustrated in FIG. 9 (with only two of the staples 57 being shown), uniformly joins the lower bowel 50 to the upper bowel 51. The ILS instrument 10 is then withdrawn through the lower bowel 50, carrying with it the excised lower end 54 of the upper bowel 51 and the excised upper end 56 of the bowel 50, as illustrated in FIG. 9.

The importance of the frictional engagement of the spool 30 on the rod 22 is readily appreciated from the foregoing description. First, the spool 30 must remain in one position on the rod 22 so as to be disposed between the anvil 14 and cartridge 15 when the instrument 10 is opened within a lumen or when the opened instrument 10 is inserted. Secondly, it is desirable that the spool 30 remain in position on the rod 22 as the surgeon feels for it and ties the tissue around it. Thirdly, it should remain on the rod 22, resisting sliding, while it draws the tissue into the cartridge 15 and the area surrounded by scalpel 18, but must then slide, without unduly stretching tissue, as the anvil 14 and rod 22 are shifted further inwardly. Such a frictional, yieldable fit is obtained by the structure as described above wherein the frictional engagement resists initial force differentials between spool 30 and rod 22.

It will be immediately appreciated that the modification to the ILS instrument 10, including the tissue retention means, such as spool 30, provides a way to enhance the anastomotic of tubular tissue structures, particularly in limited access areas such as that shown in FIG. 10 which illustrates a lower rectal resection procedure. In such procedure, the ILS instrument 10 is inserted into the rectum and the process steps mentioned above are conducted, it being unnecessary to utilize a purse-string suture in the upper end of the lower rectal stump RS. Thereafter, the upper transected bowel UB can be surgically treated. A purse string can easily be placed in the remaining portion of the bowel, where access to it is usually free, and is thereafter set over the anvil 14, as illustrated in FIG. 10, prior to drawing the anvil 14 toward the staple cartridge 15 and stapling to rejoin the bowel.

This technique includes numerous advantages. As mentioned above, it eliminates the requirement for purse-stringing of the lower rectal stump RS and as well permits the surgeon to carry out a "closed" technique, where the lower rectal stump can be closed around the ILS instrument 10 and is not open within the body during the surgical procedure. Also, the ILS instrument 10 itself is utilized to hold the rectal stump RS in an erect position for further connection to the transected bowel UB and no retention sutures are required.

Accordingly, it is unnecessary for the surgeon to spend tedious time in trying to manually produce a purse-string suture in the lower rectal stump and the procedure can be utilized when the lower rectal stump is so low that it is impossible to utilize a purse-stringing device, such as that mentioned above.

In addition to the alternative embodiments mentioned above, a number of modifications and alterations will become readily apparent. For example, it would also be possible to attach the purse-string sutured upper bowel to the same spool, rather around the rod adjacent the spool. If the spool were wide enough, it would also be possible to eliminate the purse-string suture in the upper bowel and to attach the bowel to the spool 30 in the same manner as the lower bowel. Also, it would be possible in an appropriately sized instrument, to utilize two tissue retaining means or spools, one for the lower tubular structure and one for the upper tubular structure, with no purse-string suture being required.

Of course, it will also be appreciated that the elimination of the requirement for any portion of a purse-string suture procedure will save a substantial amount of time and that the ILS instrument 10, when used in areas to which accessibility is not particularly limited, is also highly advantageous.

Accordingly, these and othr alternatives and modifications will become readily apparent to those of ordinary skill in the art, and applicant intends to be bound only by the claims appended hereto.

I claim:

1. In an intraluminal anastomotic surgical stapling instrument having a staple cartridge, a cylindrical scalpel within said cartridge, and a staple anvil mounted on a shiftable rod disposed within and extending from said staple cartridge in operable condition, said anvil being shiftable toward said staple cartridge for bringing ends of a transected tubular tissue structure together for stapling, the improvement comprising:
   tissue retention means mounted on said rod and accessible between said staple cartridge and said anvil for holding an end of a tubular tissue structure prior to and during an anastomotic procedure and wherein said tissue retention means is frictionally mounted on said rod and is yieldably slidable therealong between a first position disposed between said staple anvil and said staple cartridge for attachment of a closed tubular tissue structure thereto and a second position within said staple cartridge.

2. The improvement of claim 1, wherein said tissue retention means comprises a spool frictionally mounted on said rod against axial movement therealong and is yieldable for movement along said rod and within said cylindrical scalpel when said anvil is shifted toward said staple cartridge.

3. The improvement of claim 2, wherein said spool has an internal bore defined by a resilient surface for frictional, yieldable engagement with said rod.

4. The improvement of claim 2, wherein said spool has an internal bore receiving said rod, and within said bore elongated, axially extending, radially inwardly projecting projections frictionally engaging said rod.

5. The improvement of claim 4, wherein ends of said axially extending projections are tapered away from said rod.

6. A tissue retention spool for an intraluminal anastomotic surgical stapling instrument, said spool having at least one flanged end extending radially outward of said spool, a cylindrical tissue retention surface including a plurality of radial tissue engaging projection means for holding said tissue against sliding thereon, said spool having an internal bore for slidably receiving a rod of said instrument, said bore comprising means for yieldably gripping said rod and wherein said yieldable gripping means comprises a plurality of axially extending, inwardly projecting lugs for engaging said rod.

7. A tissue retention spool as in claim 6, wherein ends of said lugs are tapered.

8. A tissue retention spool as in claim 6, wherein saids yieldable gripping means comprises a resilient material for frictionally gripping said rod.

9. In a method for surgical anastomosing of transected tubular tissue by stapling, including the steps of inserting the distal end of a stapling instrument into said tubular tissue, said instrument having a cylindrical staple cartridge, cylindrical scalpel therein, and a staple anvil mounted on a rod shiftable toward said cartridge, securing an end of said tissue over said cartridge, excising said tubular tissue, securing a transected end of said tubular tissue over said anvil and about said rod, shifting said anvil toward said staple cartridge, stapling said disjoined tubular tissue together, excising ends of said tubular tissue internally of said staples, and removing said instrument from said tubular tissue with at least one excised end of a tubular tissue retained on said rod, the improvement comprising the additional steps of:
after inserting the instrument, tying said tubular tissue to a spool slidably mounted on said rod;
cutting said tubular tissue distally above said spool, while retaining a proximal end of said tissue on said spool;
shifting said spool within said cylindrical scalpel when said anvil is shifted toward said staple cartridge, said spool sliding on said rod once said spool is positioned; and
retaining a least one annular portion of a cut off end of said tubular tissue on said spool when said instrument is removed.

10. In a method for attaching rectal tissue to an intraluminal anastomotic surgical stapling instrument prior to surgically resecting the lower colon wherein a rectal stump having a free upper end is joined to the lower end of a transected bowel, the steps of:
securing rectal tissue to an intraluminal anastomotic surgical stapling instrument having a staple cartridge and an anvil mounted on a rod extending from said staple cartridge, by externally wrapping a flexible means around said tissue, drawing it onto a tissue retention spool disposed between said cartridge and said anvil, and tying said flexible means to secure said tissue to said spool.

11. In a method for producing a rectal stump supported on an intraluminal anastomotic surgical stapling instrument prior to resecting the lower colon wherein a rectal stump having a free upper end is joined to the lower end of a transected bowel, the steps of:
securing rectal tissue to an intraluminal anastomotic surgical stapling instrument having a staple cartridge and an anvil mounted on a rod extending from said staple cartridge, by externally wrapping a flexible means around said tissue, drawing it onto a tissue retention spool disposed between said cartridge and said anvil, tying said flexible means to secure said tissue to said spool, and cutting off said rectal tissue above said spool, thus producing a rectal stump having a closed upper end secured to said instrument around said spool between said cartridge and said anvil.

12. In a method for resecting the lower colon wherein a rectal stump having a free upper end is joined to the lower end of a transected bowel, the steps of:
securing rectal tissue to an intraluminal anastomotic surgical stapling instrument having a staple cartridge and an anvil mounted on a rod extending from said staple cartridge, by externally wrapping a flexible means around said tissue, drawing it onto a tissue retention spool disposed between said cartridge and said anvil, and tying said flexible means to secure said tissue to said spool;
cutting off said tissue above said spool, thus producing a rectal stump having a closed upper end secured to said instrument around said spool between said cartridge and said anvil;
securing a transected upper end of the bowel over said anvil and about said rod;
extending a cylindrical scalpel over said spool;
excising an end of said rectal stump and an end of said transected bowel when said stump and bowel are stapled together above said ends, said excised ends being disposed internally of said staples; and
withdrawing said cut off ends from said rectal stump when said instrument is removed.

* * * * *